(12) United States Patent
Modavis et al.

(10) Patent No.: US 7,978,893 B2
(45) Date of Patent: Jul. 12, 2011

(54) SYSTEM AND METHOD FOR MICROPLATE IMAGE ANALYSIS

(75) Inventors: Robert A. Modavis, Painted Post, NY (US); Elvis A. Zambrano, Corning, NY (US)

(73) Assignee: Corning Incorporated, Corning, NY (US)

( * ) Notice: Subject to any disclaimer, the term of this patent is extended or adjusted under 35 U.S.C. 154(b) by 942 days.

(21) Appl. No.: 11/974,406

(22) Filed: Oct. 12, 2007

(65) Prior Publication Data

US 2009/0097013 A1  Apr. 16, 2009

(51) Int. Cl.
*G06K 9/00* (2006.01)

(52) U.S. Cl. .......... 382/128; 382/133; 435/7.1; 435/7.2; 435/283.1; 435/288.1

(58) Field of Classification Search .......... None
See application file for complete search history.

(56) References Cited

U.S. PATENT DOCUMENTS

| | | | |
|---|---|---|---|
| 6,512,868 B1 | 1/2003 | Foster et al. ............ 385/33 |
| 7,202,076 B2 | 4/2007 | Cunningham et al. ..... 435/287.2 |
| 7,217,574 B2 | 5/2007 | Pien et al. ............ 436/164 |
| 7,422,891 B2 * | 9/2008 | Cunningham ............ 435/287.2 |
| 7,435,385 B2 * | 10/2008 | Lin et al. ............ 422/82.05 |
| 7,575,939 B2 * | 8/2009 | Cunningham et al. ....... 436/524 |
| 7,576,333 B2 * | 8/2009 | Caracci et al. .......... 250/458.1 |
| 7,741,598 B2 * | 6/2010 | Modavis et al. ........ 250/227.11 |
| 7,927,822 B2 * | 4/2011 | Genick et al. ............ 435/7.2 |
| 2001/0041347 A1 * | 11/2001 | Sammak et al. ............ 435/7.23 |
| 2003/0059093 A1 * | 3/2003 | Rosania et al. ............ 382/128 |
| 2005/0227374 A1 * | 10/2005 | Cunningham ............ 436/518 |
| 2006/0141527 A1 * | 6/2006 | Caracci et al. ............ 435/7.1 |
| 2010/0105148 A1 * | 4/2010 | Caracci et al. ............ 436/164 |
| 2010/0196925 A1 * | 8/2010 | Genick et al. ............ 435/7.2 |
| 2011/0006116 A1 * | 1/2011 | Modavis et al. ............ 235/437 |

OTHER PUBLICATIONS

J.H. Zhang et al., "A Simple Statistical Parameter for Use in Evaluation and Validation of High Throughput Screening Assays", Journal of Biomolecular Screening, vol. 4, No. 2, 1999, pp. 67-73.

* cited by examiner

*Primary Examiner* — Jingge Wu
*Assistant Examiner* — Julian Brooks
(74) *Attorney, Agent, or Firm* — John L. Haack

(57) ABSTRACT

A system and a method as defined herein for scan interrogation of, for example, a label-independent-detection (LID) biosensor, such as for monitoring a surface change or an event on a biosensor for use, for example, in microplate image analysis.

20 Claims, 11 Drawing Sheets

─ 1120

For Each Well:

i.) Select array of Δλ points within signal area (i.e., a signal interrogation rectangle).

ii.) Select array of Δλ points including the expected reference area (i.e., reference interrogation rectangle).

iii.) Select array of points within the signal interrogation rectangle; designate as signal sweeping rectangle.

iv.) Select array of points within the reference interrogation rectangle; designate as reference sweeping rectangle.

v.) Superimpose the signal sweeping rectangle on a portion of the signal interrogation rectangle.

vi.) For each possible location of the signal sweeping rectangle, compute the standard deviation of the contained Δλ points.

vii.) Select the optimal location of the signal sweeping rectangle from all possible locations of the signal sweeping rectangle as the rectangle having the smallest computed standard deviation of Δλ points.

viii.) Calculate the signal median value ($M_{sig}$) of the Δλ points within the signal sweeping rectangle at the selected optimal location.

ix.) Repeat v.) - viii.) above instead for the reference sweeping rectangle and the reference interrogation rectangle to provide a reference median value ($M_{ref}$) of the Δλ points within the reference sweeping rectangle at the selected optimal location.

x.) Calculate the biosensor binding value (B = $M_{sig}$- $M_{ref}$) as in Fig. 11A.

For Each Well:

i.) Select array of $\Delta\lambda$ points within signal area (i.e., a signal interrogation rectangle).

ii.) Select array of $\Delta\lambda$ points including the expected reference area (i.e., reference interrogation rectangle).

iii.) Select array of points within the signal interrogation rectangle; designate as signal sweeping rectangle.

iv.) Select array of points within the reference interrogation rectangle; designate as reference sweeping rectangle.

v.) Superimpose the signal sweeping rectangle on a portion of the signal interrogation rectangle.

vi.) For each possible location of the signal sweeping rectangle, compute the standard deviation of the contained $\Delta\lambda$ points.

vii.) Select the optimal location of the signal sweeping rectangle from all possible locations of the signal sweeping rectangle as the rectangle having the smallest computed standard deviation of $\Delta\lambda$ points.

viii.) Calculate the signal median value ($M_{sig}$) of the $\Delta\lambda$ points within the signal sweeping rectangle at the selected optimal location.

ix.) Repeat v.) - viii.) above instead for the reference sweeping rectangle and the reference interrogation rectangle to provide a reference median value ($M_{ref}$) of the $\Delta\lambda$ points within the reference sweeping rectangle at the selected optimal location.

x.) Calculate the biosensor binding value ($B = M_{sig} - M_{ref}$) as in Fig. 11A.

US 7,978,893 B2

SYSTEM AND METHOD FOR MICROPLATE IMAGE ANALYSIS

The entire disclosure of any publications, patents, and patent documents mentioned herein are incorporated by reference.

BACKGROUND

The disclosure relates to the field of biosensors for label independent detection (LID). More particularly the disclosure relates to scanning label independent detection (SLID) biosensors and to a system and method for microplate image analysis.

SUMMARY

The disclosure provides a system and method for microplate image analysis for use, for example, in SLID biosensors.

BRIEF DESCRIPTION OF THE DRAWINGS

FIGS. 11A and 11B provides a flow chart summary of the method for calculating the binding value, in embodiments of the disclosure.

DETAILED DESCRIPTION

Figure 1:
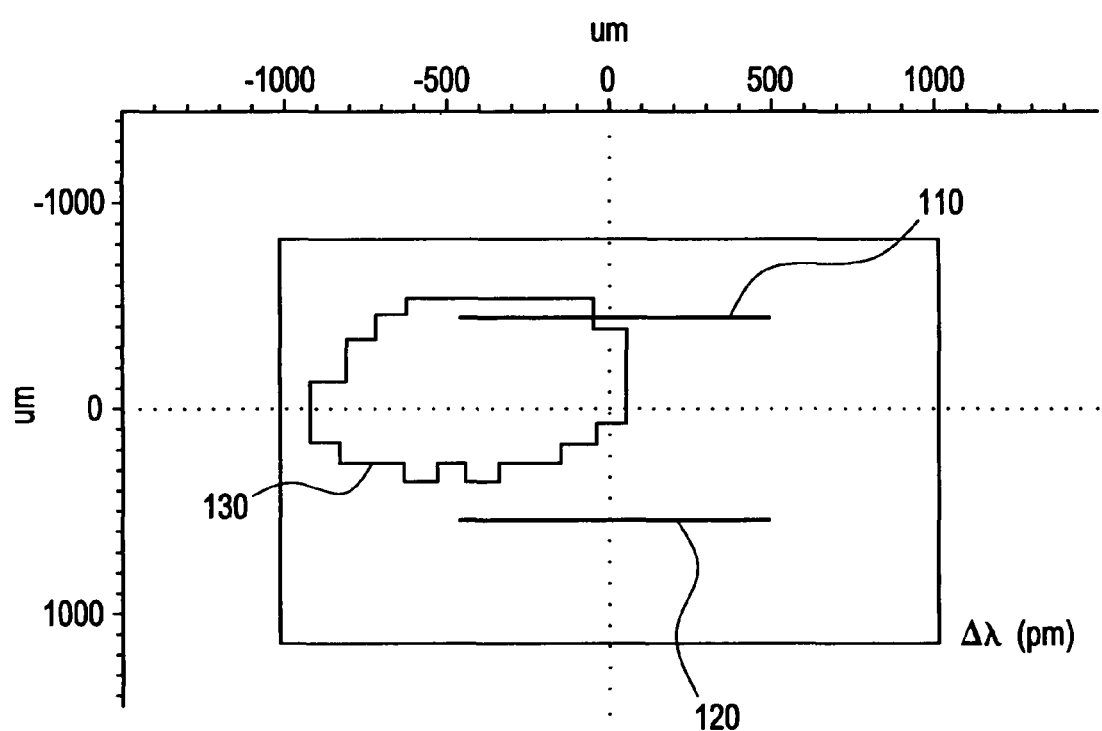
FIG. 1 shows a comparative two dimensional Δλ map of a well used a 1D dual scan technique in a microplate, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

DEFINITIONS

"Scan," "scanning," or like terms refer, for example, to a raster image data sample.

"Develop," "developed," or like terms refer, for example, to a previously unused microplate or like substrate that is or has been contacted with a substance to create or test for an interaction between the microplate surface and the substance.

"Contact" or "contacting" or like terms refer to, for example, an instance of exposure by close physical contact of at least one substance to another substance, such as between a substrate such as the chemically or biologically modified surface of a microplate and a second substance such as an analyte or a ligand.

"Attach," "attachment," "adhere," "adhered," "immobilized," or like terms generally refer to immobilizing or fixing for example, by any physical-chemical interaction between two or more components or compounds, for example, a protein or like synthetic or natural biological, a surface modifier substance, a compatibilizer, a cell, a ligand candidate compound, and like entities within the scope of the disclosure, such as to a surface, such as by physical absorption, chemical bonding, and like attachment interactions, or combinations thereof. Examples of attachment interactions can include, for example, covalent, electrostatic, ionic, hydrogen, hydrophobic bonding, and like interactions, or combinations thereof. The type and extent of physical-chemical interaction that can be formed will vary depending upon the starting materials that are selected or probed for and interaction conditions.

The indefinite article "a" or "an" and its corresponding definite article "the" as used herein means at least one, or one or more, unless specified otherwise.

"Include," "includes," or like terms means including but not limited to.

"About" modifying, for example, the quantity of an ingredient in a composition or a sample, concentrations, volumes, process temperature, process time, yields, flow rates, pressures, or like values, and ranges thereof, employed in describing the embodiments of the disclosure, refers to variation in the numerical quantity that can occur, for example, through typical measuring and computational procedures used for scanning; through inadvertent or systematic errors in these procedures; through differences in the manufacture, source, or purity of materials used to carry out the methods; and like considerations. The term "about" also encompasses amounts that differ due to, for example, aging of a microplate formulation having a particular initial concentration, mixture, or surface topography, and amounts that differ due to processing a formulation with a particular initial concentration, mixture, or surface topography. Whether modified by the term "about" the claims appended hereto include equivalents to these quantities.

"Optional" or "optionally" or like terms generally refer to, for example, that the subsequently described event or circumstance can or cannot occur, and that the description includes instances where the event or circumstance occurs and instances where it does not.

"Consisting essentially of" in embodiments refers, for example, to a microplate surface composition or disposition, a system and method for measuring microplate surface composition or disposition, a system and method for measuring differences in microplate surface composition or disposition, a system and method for microplate image analysis, such as a biosensor in a microplate, and articles, devices, or apparatus of the disclosure, and can include the components or steps listed in the claim, plus other components or steps that do not materially affect the basic and novel properties of the composition, article, apparatus, system, and method of making and use of the disclosure, such as a particular reactant, a particular additive or ingredient, a particular agent, a particular surface modifier or condition, a particular ligand candidate, a particular equation or mathematical expression, or like structure, material, process, or computational variable selected. Items that may materially affect the basic properties of the components or steps of the disclosure, or that may impart undesirable characteristics to aspects of the present disclosure include, for example, an increase in the number of data point outliers; decreased data quality (e.g., low Z' statistic); increased instrument noise; increased sensitivity to the location of the reference pads; decreased confidence in the binding calculation; and increased probability for false negatives and false positives for a given threshold level, or like characteristics.

Thus, the claimed invention may suitably comprise, consist of, or consist essentially of: a method for microplate image analysis as defined herein; and a system for SLID as defined herein including an optical biosensor having a microplate, associated biosensor scan optics, and an image processor for computing image biosensor binding values according to the microplate image analysis method.

This application is related in certain aspects to the following commonly owned and assigned patent applications:

U.S. patent application Ser. No. 11/027,547, filed Dec. 29, 2004, entitled "Spatially Scanned Optical Reader System and Method for Using Same", Publication No. US 20060141611 A1, published Jun. 29, 2006.

U.S. patent application Ser. No. 11/027,509, filed Dec. 29, 2004, entitled "Method for Creating a Reference Region and a Sample Region on a Biosensor and the Resulting Biosensor", Publication No. US 20040141527 A1, published Jun. 29, 2006, see for example FIG. 1 which illustrates three different methods for creating a reference region and a sample region on a single biosensor.

U.S. patent application Ser. No. 11/210,920, filed Aug. 23, 2005, entitled "Optical Reader System and Method for Monitoring and Correcting Lateral and Angular Misalignments of Label Independent Biosensors", Publication No. US 20060139641 A1, published Jun. 29, 2006, mentions an optical reader system that uses a scanned optical beam to interrogate a biosensor to determine if a biomolecular binding event occurred on a surface of the biosensor. In embodiments, the optical reader system includes a light source, a detector and a processor (e.g., computer, DSP). The light source outputs an optical beam which is scanned across a moving biosensor and while this is happening the detector collects the optical beam which has been reflected from the biosensor. The computer processes the collected optical beam and records the resulting raw spectral or angle data which is a function of a position (and possibly time) on the biosensor. The processor can then analyze the raw data to create a spatial map of resonant wavelength (peak position) or resonant angle which indicates whether or not a biomolecular binding event occurred on the biosensor. Several other uses of the raw data are also described.

U.S. Patent Application Ser. No. 60/781,397, filed Mar. 10, 2006, entitled "Optimized Method for LID Biosensor Resonance Detection," now U.S. patent application Ser. No. 11/716,425, filed Mar. 9, 2007.

U.S. Patent Application Ser. No. 60/844,736, filed Sep. 9, 2006, entitled "Active Microplate Position Correction for Biosensors."

U.S. patent application Ser. No. 11/711,207, filed Feb. 27, 2007, entitled "Swept Wavelength Imaging Optical Interrogation System and Method for Using Same."

In embodiments the disclosure provides a method and system for microplate scan analysis. In embodiments, the method and system can improve the performance of, for example, the Corning® Epic® analyzer, an automated biosensor system platform, using a superior microplate scan and data analysis method. The method and system of the present disclosure, while having been demonstrated as being particularly useful, for example, in the Corning® Epic® analyzer, the method and system can be useful, for example, in any apparatus or method that resolves 1D or 2D spatial data, such as in image processing, and like applications.

System and Method

Described are a system and method for biosensor substrate image analysis which system and method are useful for performing, for example, diagnostic or therapeutic assays such as for scanning label independent detection. In embodiments one or more biosensors can be situated in a well of a microplate and the disclosed system and method can interrogate one or more of the biosensors to provide binding information between the biosensor surface, such as an immobilized cell and a binding target or partner.

In embodiments the disclosure provides a method for analyzing a biosensor, for example, for the purpose of determining biosensor binding, the method comprising:

scanning an area of the biosensor;

selecting a first-limit signal-region and a second-limit reference-region within the scanned area;

scanning at least one sub-region within the first-limit signal-region and at least one sub-region within the second-limit reference-region;

calculating a standard deviation for all $\Delta\lambda$ points scanned in each sub-region;

selecting all sampled points within each of the scanned sub-regions having a minimum standard deviation as a signal sub-region and as a reference sub-region; and calculating $M_{sig}$, $M_{ref}$, and $B_{med}$, where, for example, at least one signal sub-region has a minimum standard deviation signal sub-region, at least one reference sub-region has a minimum standard deviation, a $\Delta\lambda$ point is the difference in wavelength at a point for two different time points according to $\Delta\lambda = \pi_{t1} - \lambda_{t1}$, where $\lambda_{t2}$ and $\lambda_{t1}$ represent the wavelengths measured for the respective second and first time points, $M_{sig}$ is the median value of all $\Delta\lambda$ points in the optimal, that is, the selected minimum signal sub-region, $M_{ref}$ is the median value of all $\Delta\lambda$ points in the optimal, that is, the selected minimum reference sub-region, and $B_{med}$ is the median biosensor binding value according to equation (1):

$$B_{med} = M_{sig} - M_{ref} \tag{1}$$

In embodiments, the biosensor contact surface can be, for example, undeveloped. Thus, the method of the disclosure can provide a useful tool for determining, for example, baseline or reference data relating to the quality of a biosensor in neat, undeveloped, or unused microplates, or like manufactured surfaces. Additionally or alternatively, the biosensor contact surface can be developed. Thus, for example, the method of the disclosure can be a useful tool for determining, for example, the quality of the data obtained from a biosensor in a microplate in, for example, a chemical, pharmacological, biological, or like assay.

In embodiments, the selected first-limit signal-region and the second-limit reference-region within the scanned area can be mutually exclusive. In embodiments, the scanning of a sub-region within the first-limit signal-region and the second-limit reference-region can include a plurality of sub-regions within each of the first-limit signal-region and the second-limit reference-region. The plurality of sub-regions within the first-limit signal-region and the second-limit reference-region can each comprise, for example, from about 1 to about 10,000 sub-regions, from about 1 to about 1,000 sub-regions, from about 2 to about 500 sub-regions, and from about 10 to about 100 sub-regions. In embodiments that employ a one-dimensional limit approach, that is a sweep rectangle having a "zero height," the plurality of sub-regions within the first-limit signal-region and the second-limit reference-region can each comprise, for example, the above mentioned sub-region ranges, and for example, from about 1 to about 10 sub-regions. The foregoing one-dimensional limit "zero-height" approach is particularly applicable in, for example, single sweep, rapid scan, or rapid analysis embodiments. The biosensor can comprise, for example, a plurality of biosensors within a microplate, such as having 96- or 384-wells, or similar count wells including single wells, multi-wells and compound wells. Additionally or alternatively, the biosensor can comprise any other suitable format.

In embodiments, the disclosed method can readily provide results having a Z' statistic of from about 0.5 to about 0.95, and from about 0.6 to about 0.99, such as when outliers are excluded.

In embodiments, the disclosure provides a method for analyzing a biosensor to determine, for example, the presence and extent of biosensor binding, the method comprising:

scanning an area of the biosensor;

selecting a first-limit signal-region and a second-limit reference-region within the scanned area;

scanning at least one sub-region within the first-limit signal-region and at least one sub-region within the second-limit reference-region;

calculating a standard deviation for all Δλ points scanned in each sub-region;

selecting all sampled points within each of the scanned sub-regions having a minimum standard deviation as a signal sub-region and as a reference sub-region; and calculating $A_{sig}$, $A_{ref}$, and $B_{ave}$, where, for example, at least one signal sub-region has a minimum standard deviation for the scanned signal sub-regions, at least one reference sub-region has a minimum standard deviation for the scanned reference sub-regions, that is a minimally variable or optimal sub-region for each of the signal and reference scanned regions is identified for selection, a Δλ point is the difference in wavelength at a point for two different time points according to $\Delta\lambda = \lambda = \lambda_{t2} - \lambda_{t1}$ where $\lambda_{t2}$ and $\lambda_{t1}$ represent the wavelengths measured for the respective second and first time points, $A_{sig}$ is the average value of all Δλ points in the selected minimum signal sub-region, $A_{ref}$ is the average value of all Δλ points in the selected minimum reference sub-region, and $B_{ave}$ is the averaged biosensor binding value according to equation (2):

$$B_{ave} = A_{sig} - A_{ref} \quad (2).$$

In embodiments, the disclosure provides a system to determine biosensor binding, the system comprising:

a microplate comprising a frame including a plurality of wells formed therein, each well incorporating a biosensor having a surface with a reference region and a sample region;

an optical reader interrogator comprising an optical beam and optics for illuminating a portion of the biosensor, image optics for receiving reflected light from the illuminated biosensor, and a 2D imaging device for capturing a sequence of images from the illuminated biosensor; and a processor to process the acquired scanned data in accordance with any of the methods of the disclosure.

In embodiments, the disclosure provides an optical interrogation system comprising:

an illuminator that emits an optical beam towards a biosensor;

a receiver that collects an optical beam from the biosensor and then outputs a signal which corresponds to the collected optical beam; and a processor to process the signal to determine biosensor binding in accordance with any of the methods of the disclosure.

In embodiments, the processor can be, for example, a programmable computer, a digital signal processor (DSP), or like devices for calculating, computing, comparing, selecting, or like operations of the system and the method.

In embodiments of the disclosure, a Corning Epic® label-independent detection system can be used as a label-independent biochemical binding detection system. It can consist of a 384-well microplate with optical biosensors within each well, and an optical reader to interrogate these microplates. Each well can contain a small e.g., about 2 mm×2 mm) optical grating, known as a resonant waveguide grating (RWG). The wavelength of the light reflected by the grating is a sensitive function of the optical refractive index at the surface of the sensor inside the well. Hence when material such as a protein, antibody, drug, cell, or like material binds to the well bottom or sensor surface, the reflected wavelength will change.

The optical reader, referred to as SLID for scanned label-independent detection, uses a series of focused optical beams that are scanned across the bottom of the microplate to measure reflected wavelength from each optical sensor. The reader may be used to monitor changes in the reflected wavelength from each sensor as a function of time. It may also be used to evaluate wavelength or changes in wavelength as a function of position within each sensor, that is, spatially resolved or imaging information.

When biochemical material binds to the surface of a sensor, this alters the local refractive index, and the wavelength reflected by the optical sensor changes. The reader detects and quantifies this wavelength change in order to measure biochemical events within each well. Light that impinges upon the sensor is resonantly coupled into the waveguide only if it has the appropriate combination of wavelength and incident angle (i.e., wave vector.)

By monitoring the reflected wavelength (or angle) as a function of time, one may determine if material has bound to or been removed from the surface of the sensor. A typical assay is performed by first immobilizing, for example, a protein to the surface of microplate. Then a baseline read is performed where the wavelength reflected by each of the sensors in the plate is measured and recorded. Then a binding compound (e.g., a drug compound or candidate) is added to the wells, and a second wavelength read is made. The wavelength shift that occurs between the two reads is then a measure of how much drug has bound to each sensor of the microplate.

Often a portion of each sensor can be chemically or physically blocked to prevent binding, to act as a reference signal for removing false wavelength shifts that arise from environmental changes such as bulk refractive index changes, material drift, non-specific compound binding, thermal events, or like events. The interrogation system must be able to distinguish the signals from the binding and reference regions, each of which may occur at almost any wavelength within the sensor bandwidth, and are of the same polarization. In embodiments, intra-well references, where a small portion of each well can be chemically blocked can act as a spatially local reference.

Figure 8A:
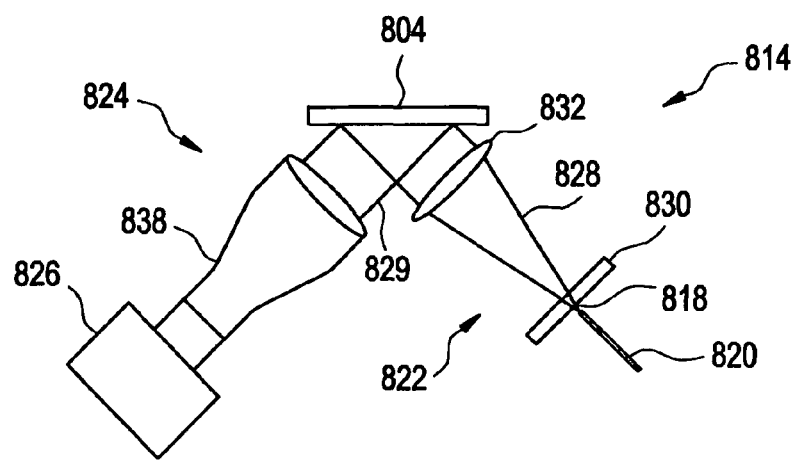
FIGS. 8A and 8B show aspects of an imaging system of an SLID optical reader system, in embodiments of the disclosure.

Referring to FIG. 8A there is an exemplary imaging system 814 shown having an oblique incidence configuration in accordance with another embodiment of the disclosure (reference the abovementioned U.S. Ser. No. 11/711,207). The oblique incidence angle eliminates the need for a beam splitter and can improve the optical efficiency by a factor of 4. In this embodiment, the imaging system 814 has illumination optics 822 including a lens optic 830 which receives the optical beam 818 and outputs an interrogation beam 828 at a predetermined angle towards a collimating lens 832. The collimating lens 832 receives the interrogation beam 828 and outputs the collimated interrogation beam 828 which illuminates a predetermined number of biosensors 802 located within the wells of the microplate 804. Alternatively, the illumination optics 822 can be configured to convert the received optical beam 818 into multiple interrogation beams 828 where each interrogation beam 828 would illuminate a corresponding biosensor 802 located within the well of the microplate 804. In addition, the imaging system 814 has a telecentric lens 838 which is positioned at a predetermined angle and has a field of view that was specifically selected to collect an image 829 from the illuminated biosensor(s). Lastly, the imaging system 814 has 2-D imaging device 826, attached to the telecentric lens 838, which takes/collects a sequence of pictures/images 829 of the illuminated biosensor(s) on the microplate 804. Each picture/image 829 corresponds with a different wavelength of the optical beam 818 or interrogation beam 828.

Figure 8B:
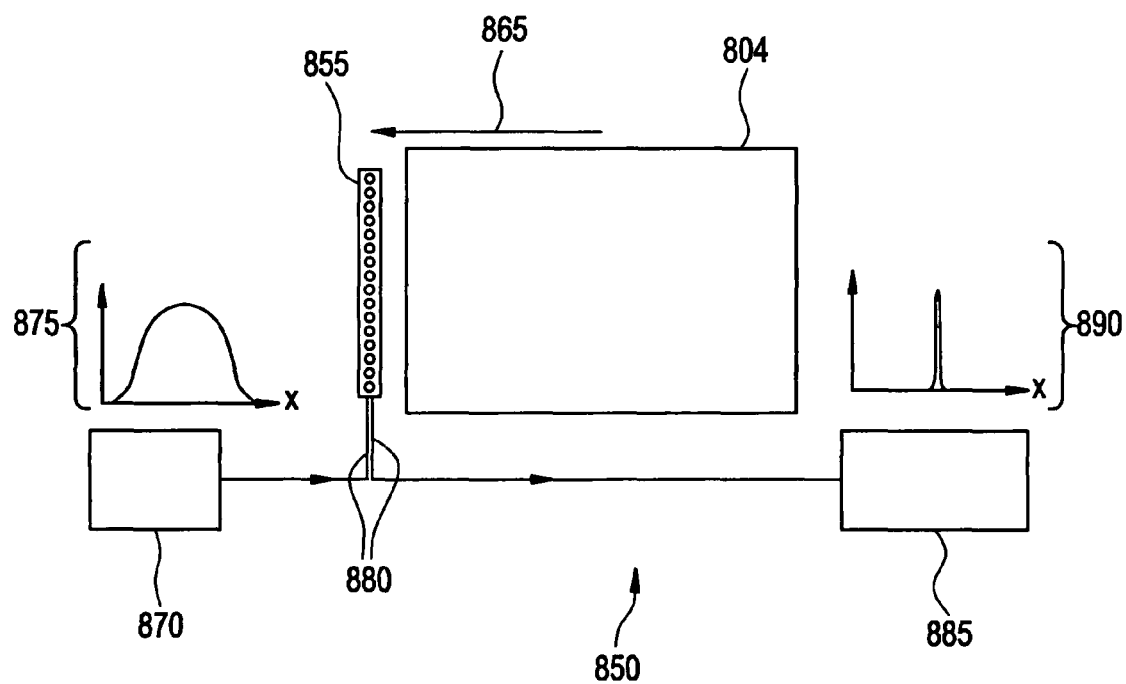

Referring to FIG. 8B there is shown an exemplary SLID reader 850 having a lense array 855 with, for example, a series of 16 optical beams, one for each biosensor row (not shown) on the microplate 804. The microplate 804 can be scanned across lense array 855 in the direction 865. A light source 870 having, for example, a broadband spectrum 875 (power v. wavelength) illuminates the lense array and the microplate 804. The lense array delivers light via optical fibers 880. The lense array also receives or acquires reflected resonance light and transmits wavelength and power information (power v. λ curve) 890 as a function of position within each well via optical fibers 880 to spectrometer(s) 885. A processor processes the information 890 to output a binding signal (wavelength change) as a function of time. In the configuration shown the light beams can strike the plate from below at normal incidence, and the spot size is nominally 100 micrometers ($1/e^2$ diameter). Other suitable incidences can be used.

Figure 9:
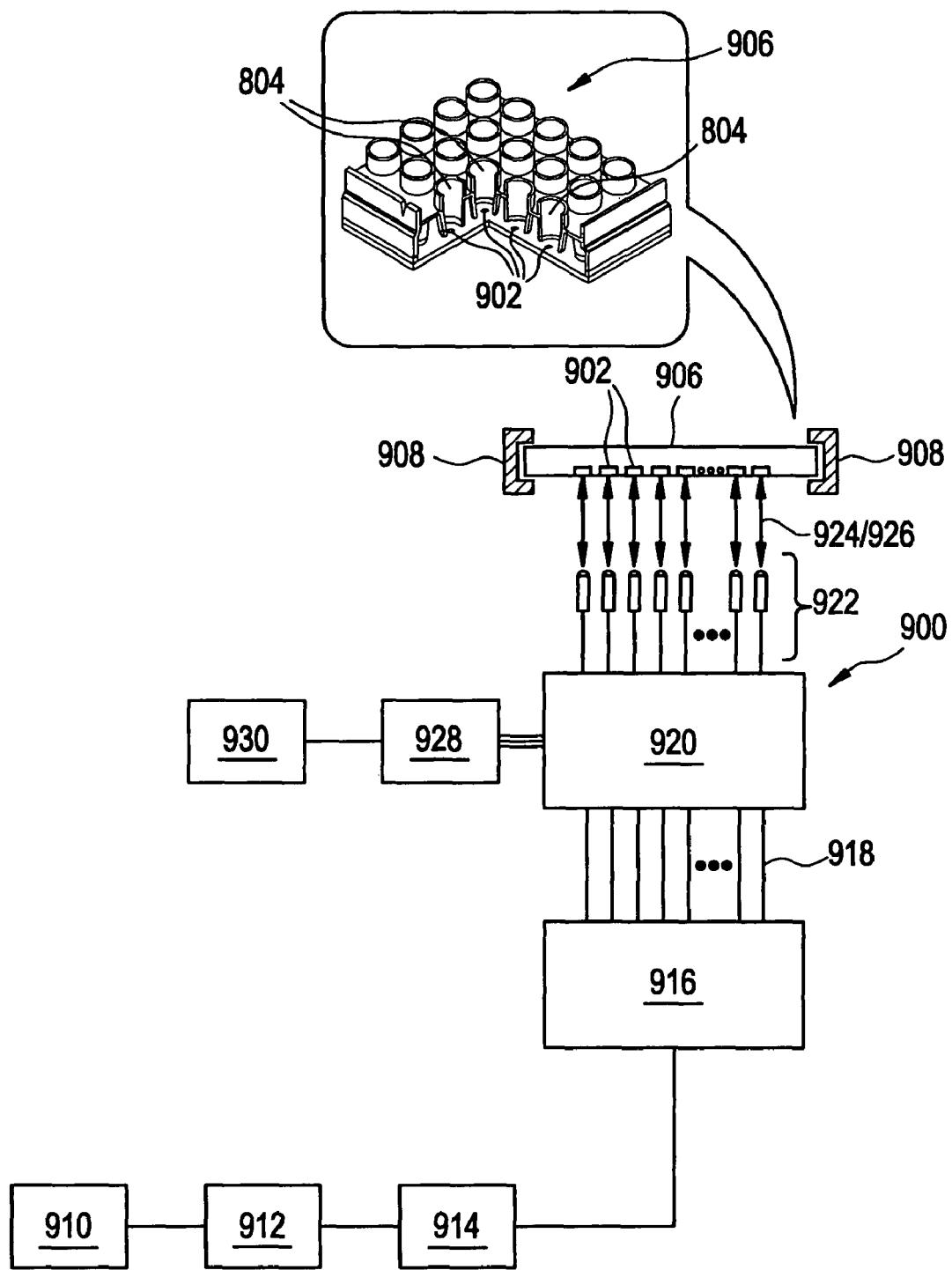
FIG. 9 shows exemplary optical reader system componentry, in embodiments of the disclosure.

Referring to FIG. 9, there is shown in greater detail a schematic of an exemplary optical interrogation system 900 and associated optical reader system componentry which is capable of interrogating biosensors 902 located within the wells 904 of a microplate 906 that is placed on a holder 908 (XY translation stage 908). The discussion below refers to a 384-well microplate 906, however, any other suitable microplate format can be used. The optical interrogation system 900 includes a light source 910 (e.g., superluminescent diode (SLD)) which is fiber pigtailed and connected to a variable optical attenuator (VOA) 912 that is connected to a polarization scrambler 914. The polarization scrambler 914 outputs a light beam which is split by a 1×16 splitter 916 into 16 individual optical fibers 918. A 1×2 splitter array 920 having 16 channels connects each optical fiber 918 to one of 16 fiber microlenses 922 as shown in FIG. 8a. Each fiber microlense 922 (which has for example a single mode fiber) delivers a light beam 924 to a moving biosensor 902 (or static biosensor 902) and also receives a reflected light beam 926. The reflected light beam 926 passes through the 1×2 splitter array 920 and is detected by one of sixteen spectrometers 928. Each spectrometer 928 (optical detection system 928) collects the raw spectral data (interrogation measurements) in the reflected light beam 926 and this raw spectral data is read-out by a personal computer (PC) 930. The PC 930 records the raw spectral data/interrogation measurements as a function of the position of the holder 908 (XY translation stage 908). In addition, the PC 930 analyzes the raw spectral data (interrogation wavelength/angular measurements) which can detect and account for any positional misalignment of a re-positioned microplate 906 and interrogate the biosensors 902. In this interrogation system 900, a wide spectrum light source 910 can be used to illuminate the biosensors 902 and the PC 930 can be used to analyze the resonance spectral content of the normal retro-reflected light beams 926. Alternatively or additionally, if desired an angular optical interrogation system could be used to implement the disclosed method. As shown in FIG. 9, the microplate 906 can be moved across a fixed optical head (not shown) which holds 16 fiber microlenses 922 and each fiber microlense 922 emits one optical beam 924 which interrogates the biosensors 902 in one row on the microplate 906. A precision X/Y translation stage 908 can be used to move the microplate 906. A typical 384-well format microplate 906 is, for example, approximately 3 inches in width and 5 inches in length. Hence, to read the entire microplate 906, the X/Y translation stage 908 may move up to 125 mm in distance along the x dimension of the microplate 906, but typically less than 4.5 mm in the y-dimension since 16 lenses 922 are linearly arranged along the y-dimension. In this example, the X/Y translation stage 908 contains an optical encoder that provides pulses for every 200 nm of motion. The PC 930 tracks and records these pulses so that the absolute position of the X/Y translation stage 908 holding the microplate 906 is known at any given time during the interrogation of the biosensors 902 within the microplate 906.

Thus, in embodiments, a broadband superluminescent diode (SLD) light source can be coupled into a single mode optical fiber. The light is then sent through a polarization scrambling element, and a variable optical attenuator (VOA) to allow for power control. Light can then be split into 16 fibers that ultimately feed light into the 16 optical lenses. A 1×2 fiber optical splitter can be positioned just before each lens, to allow retro-reflected light to be redirected to a series of spectrometers. Each spectrometer monitors the light reflected back from one lens, which in turn interrogates one row of the microplate as the plate is scanned across the optics. Isolator optics can optionally be placed on top of the lenses to suppress Fresnel (non-resonant) reflections. As a given optical beam traverses a grating, an optical spectrum is captured. This spectrum contains an optical resonance. The centroid (nominal wavelength) of this resonance is measured, along with the peak amplitude. A typical observed resonance on this system has a FWHM of, for example, 850-1,000 pm with the UVCC Epic® sensors. The wavelength and peak power are then recorded as a function of time as the beams are scanned across each grating. If one knows the spatial pattern of the scan, this time information can be converted into (x,y) position (a spatial pixel).

In embodiments, the optical beams may be scanned in any other suitable manner. For example, the scans may take a 1D slice across a grating, they can be raster scanned to produce a 2D image, or like patterns, and combinations thereof. The format of the spatial scan can be readily changed by the user if desired via the reader software.

The aforementioned imaging reader system has a spatial resolution determined by the optical beam size (e.g., 100 microns 1/e2 or 58 microns FWHM). Regions of arbitrary size and shape may be averaged together. This may be done after data has been acquired such as in a post-processing technique. Thus, the sensors can be re-analyzed in multiple ways once data is acquired. Accordingly, the SLID reader architecture provides solutions to a number of technical problems, including for example:

wide angular tolerance provides for rapid scanning of plates that can be accomplished without realignment;

image based scanning provides spectra and wavelength information that can be selectively acquired and processed for specific regions of the wells enabling co-located self-reference and signal (binding) regions within the same well where thermal effects can be minimized; and the translation sensitivity of the system can also be reduced, or at least mitigated, relative to a small spot size system, since a large area may be assembled (averaged) from a series of pixels, an effectively larger beam size may be created, which reduces the impact of micro-scale wavelength roughness of the sensor.

Figure 10:
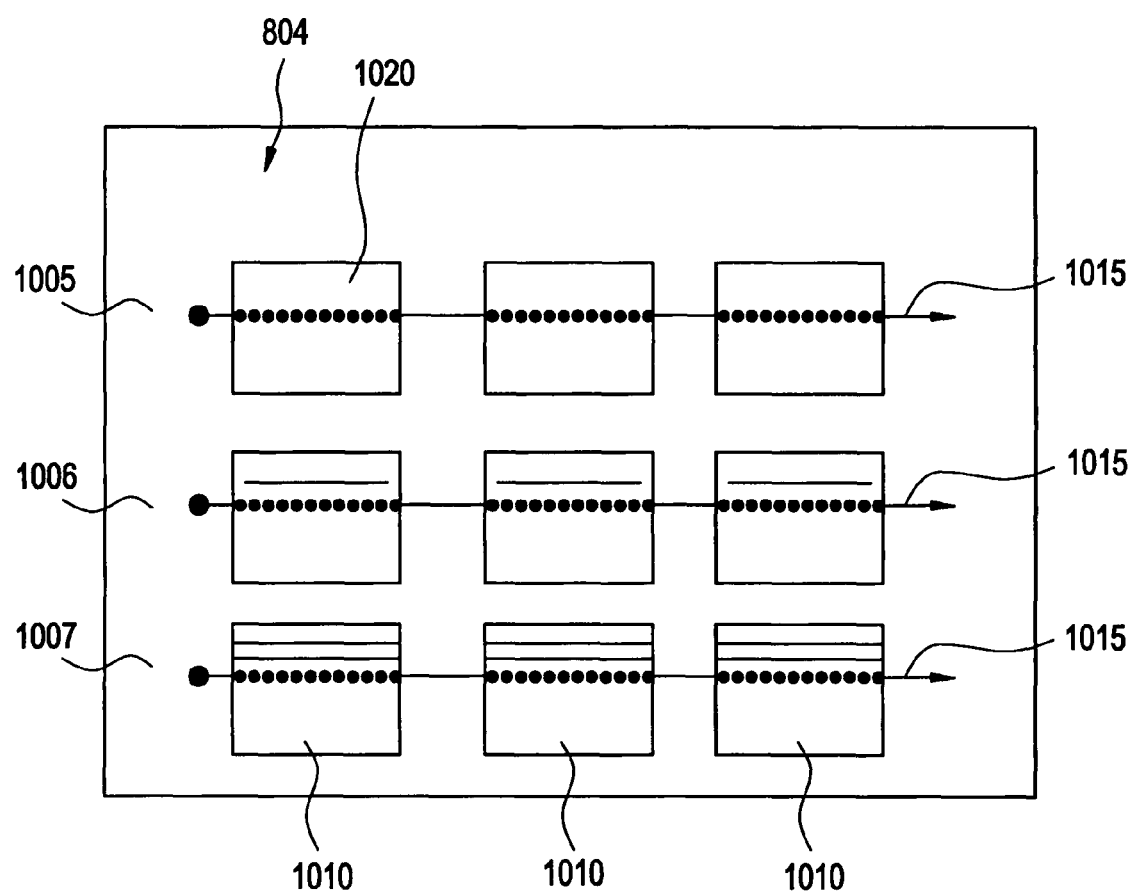
FIG. 10 illustrates an example of how a SLID optical system acquires scan data from a microplate, in embodiments of the disclosure.

FIG. 10 illustrates an example of how a SLID optical system acquires data from a portion of microplate 804. A series of simultaneous or sequential optical beams 1005, 1006, 1007, . . . etc. (e.g., 16 beams designated A, B, C, . . . etc.) are initially (first time $t_1$) scanned across biosensor gratings 1010 in scan direction 1015, and spectra are recorded and processed as a function of position such as a series of coordinated points (x,y) 1020 across a row of biosensors. The same positional scans are then repeated at a later time (second time $t_2$), and the measured wavelengths are compared to the values found in the initial or earlier scans, to evaluate binding as a function of time.

The Corning Epic® label-independent detection system can include an optical reader that interrogates, for example, microplates containing resonant waveguide grating biosensors, and evaluates biochemical binding on the sensors by detecting spectral shifts in reflected wavelength. The magnitude of these wavelength shifts can be, for example, from about 2,000 picometers (pm) for large protein/antibody interaction or attachment to about 1 pm for small drug binding. A scanned label-independent detection (SLID) reader translates small (such as less than 100 microns) diameter optical beams across the microplate, and obtains spatially resolved wavelength data in either one or two dimensions from each well. In embodiments, a super-luminescent diode light source can be used to illuminate the sensors and spectrometers to measure the reflected resonance wavelength. As an imaging reader, it can use plates with chemically blocked (reference) sub-regions, or with patterns of protein within the wells (signal) sub-regions. In embodiments, the reader can also actively control the microplate position to, for example, less than about 200 nanometers to minimize wavelength shifts induced by plate removal events, see for example the aforementioned U.S. patent application Ser. Nos. 11/210,920, and 60/844, 736. The system can accomplish high-throughput screening methods, such as for drug compounds, including having excellent sensitivity (e.g., detecting about 1 pm level binding events), read speed (e.g., about 1 minute per plate read), and plate in/out capability. This system can incorporate various design considerations or options, optical system components, noise performance, and operational modes.

Figure 11A:
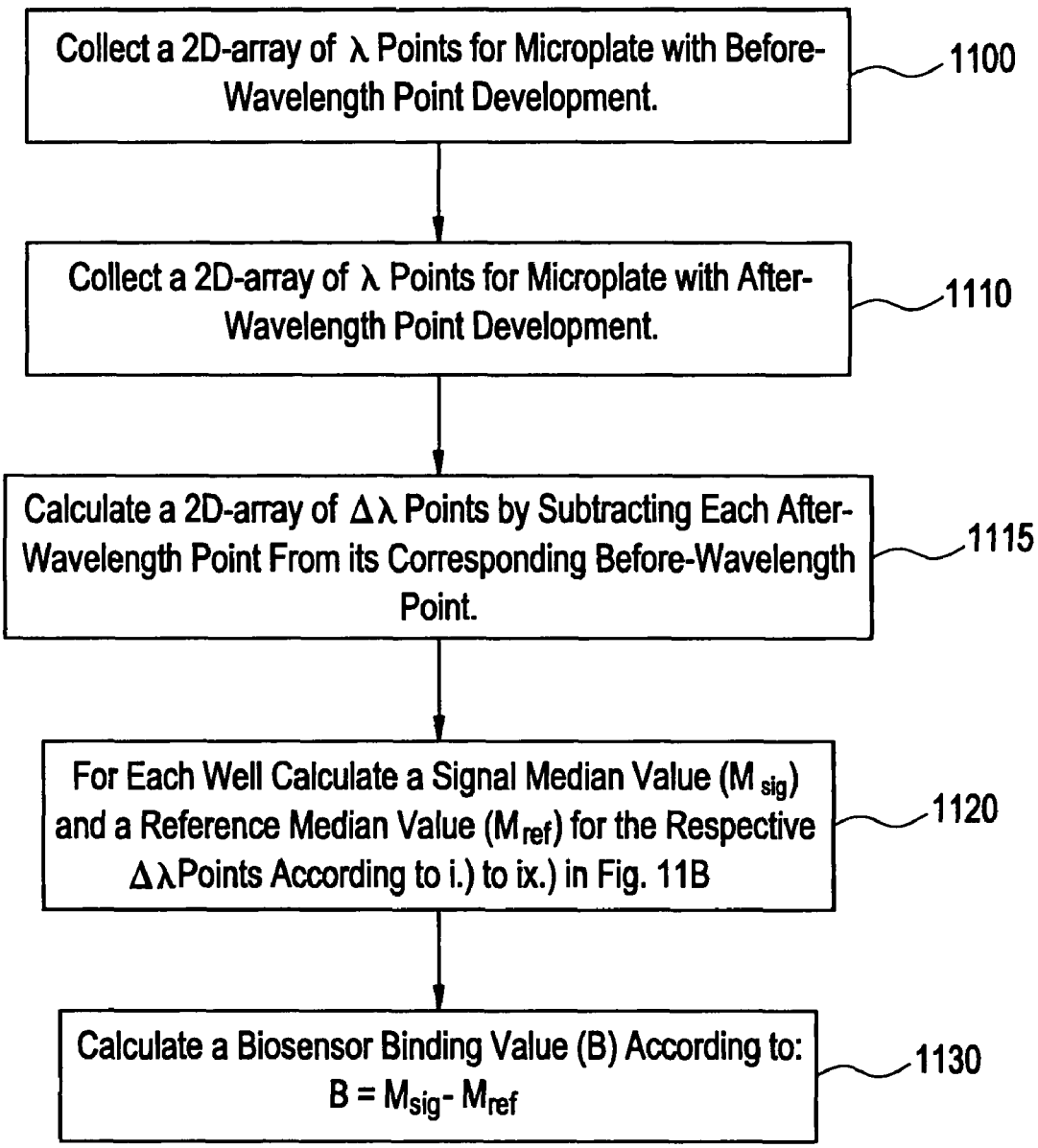

In embodiments, the method of the disclosure is further illustrated and described below including the working examples. FIGS. 11A and 11B provides a step-wise flow chart summarizing the method for calculating the binding value from the scanned data. FIG. 11A summarizes the acquisition and calculation of 2D-array of λ points for microplate wells from the difference in before-wavelength point development and after-wavelength point development. Thus, the system and method collects a 2D-array of λ points for microplate wells before-wavelength point development 1100, then collects a 2D-array of λ points for microplate wells after-wavelength point development 1110, and then calculates a 2D-array of Δλ points by subtracting each after-wavelength point from its corresponding before-wavelength point 1115.

For each well there is calculated a signal median value ($M_{sig}$) and a reference median value ($M_{ref}$) for the respective Δλ points according to i.) through ix.) below and in FIG. 11B (1120). Thereafter a median biosensor binding value (B) is calculated according to the difference in median values: $B=M_{sig}-M_{ref}$ (1130). Subroutine steps i.) through ix.) for each well are summarized below and in FIG. 11B (1120).

i.) Selecting an array of Δλ points within the signal area or region (i.e., a signal interrogation rectangle or limit signal-region).

ii.) Selecting an array of Δλ points that includes the expected reference area (i.e., reference interrogation rectangle or limit reference-region).

iii.) Selecting an array of points within the signal interrogation rectangle (designated as a signal sweeping rectangle or signal sub-region).

iv.) Selecting an array of points within the reference interrogation rectangle, (designated as a reference sweeping rectangle or reference sub-region).

v.) Superimposing the selected signal sweeping rectangle and its corresponding array points on a portion of the signal interrogation rectangle.

vi.) Computing the standard deviation of the contained Δλ points for each possible location of the signal sweeping rectangle.

vii.) Selecting an optimal or minimized location of the signal sweeping rectangle from all possible locations of the signal sweeping rectangle as the sweep rectangle having the smallest computed or calculated standard deviation of its Δλ points, i.e., a selected minimum.

viii.) Computing the signal median value ($M_{sig}$) of the Δλ points within the signal sweeping rectangle at the selected minimized location.

ix.) Repeating the above subroutine steps v.)—viii.) for the reference sweep rectangle and the reference interrogation rectangle to provide a reference median value ($M_{ref}$) of the Δλ points within the reference sweeping rectangle at the selected minimized location.

x.) Finally, calculating the median biosensor binding value ($B=M_{sig}-M_{ref}$) as in FIG. 11A (1130).

Although selection of a rectangular array is specifically mentioned in the above exemplary description, other suitable geometries for the array can be selected, for example, square, circle, triangle, parallelogram, trapezoid, or like shapes, and combinations thereof.

Similarly and as disclosed herein, an alternative embodiment provides a method determining average biosensor binding values based on calculating the average biosensor binding value according to $B_{ave}=A_{sig}-A_{ref}$.

Although this disclosure may be useful for detection using labeled ligands it is particularly well suited for biosensors based on label-free or label independent detection (LID) methods such as a resonant waveguide (RWG) optical biosensor, for example, the Corning Incorporated's Epic® system or those based on surface plasmon resonance (SPR).

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

A commercially available instrument, such as the Corning® Epic® analyzer uses a one-dimensional (1D), dual scan method which scans a short linear region of both the signal part of the well and the reference part of the well. In embodiments, the disclosed method is suitable for use in one-dimensional (1D) scan region routines, for example, having limit-rectangles and sweep-rectangles with zero-height, such as where the scan reduces to an x-scan line instead of an x-y scan rectangle. In embodiments, the disclosed method is suitable for use in two-dimensional (2D) scan region routines encompassing a signal area and a 2D region including at least the reference area and optionally a "surround," that is an area immediately surrounding or bordering the reference area. By searching for and selecting the most uniform sub-region in these scanned areas, defects can be avoided and the accuracy of the measurement is improved. In addition, a reference pad can be located by the disclosed search method which reduces the tolerances on where the reference pad can be located, which can provide improvements in microplate manufacture, for example, cost reductions and production efficiency enhancements, since reduced tolerances translate into fewer rejects or scrap and leads to higher overall yields.

A 2D analysis method was developed for processing data collected by a reader in, for example, a Corning® Epic® instrument. The reader measures the resonant wavelengths of a microplate at selected spatial locations. The method is more insensitive to defects in the well compared to a comparative 1D dual scan method so that the sensitivity of the instrument and the analysis is increased. The disclosed method searches for the location of the reference pad and enables reduced tolerances on its placement and increases the ease and reliability of manufacture.

A 1D dual scan method was compared with a 2D sweep method for analyzing microplates. The disclosed 2D method uses 2D regions for both the signal and reference regions in which the optimum signal and reference regions are found by searching. The 2D method had a number of notable advantages compared with the 1D method, including:

improved Z' values, especially for low Z' plates;
a reduced number of outliers;
a reduced probability for false negatives and false positives for a given threshold level (this aspect significantly improves the sensitivity of the measurement by approximately a factor of 2 or more);
a reduced sensitivity to the location of the reference pads; and
maximizing the number of pixels used in the binding calculation.

An increased or maximized number of pixel points in both the signal and reference regions provides reduced instrument noise since the greater the number of points used, the smaller the instrument noise becomes.

In embodiments, the limit signal-region or limit reference-region (e.g., rectangles) dimensions can be, for example, coextensive with, or greater than the sweep rectangle dimensions. In embodiments, the signal sub-region dimensions (e.g., sweep rectangles) can be, for example, at least one of: greater than, less than, or equal to (i.e., coextensive), the reference area dimensions or the signal area dimensions; in embodiments, the limit rectangle dimensions can be, for example, at least one of: greater than, less than, or equal to, the reference area dimensions or the signal area dimensions. In embodiments, the number of $\Delta\lambda$ points for each region can be larger than used for the 1D method.

Comparative Example

One Dimensional (1D) Dual-Scan Method A comparative method for scanning and analyzing data in the Epic® system uses an inferior 1D dual scan algorithm. This method scans a short (e.g., 672 µm) linear region in the signal region and the same short length linear scan across a reference region. Referring to the Figures, FIG. 1 shows a two dimensional $\Delta\lambda$ map of a well in the microplate indicating the two lines corresponding to the upper reference (110) and lower signal (120) scans. These linear paths are scanned a total of five times each and the respective results are averaged. The delta wavelength ($\Delta\lambda$) values for each point in the signal region are averaged as are all the delta wavelength ($\Delta\lambda$) values in the reference region. The difference between the averaged $\Delta\lambda$s in these respective regions gives the binding value for the well. The region (130) in the well is caused by a defect. Example defects can include, for example, bubbles in a well, clumps of non-specific binding material, a physical imperfection on the plate surface, such as a scratch, or like physical imperfection or deformity, including any other structure or surface feature that provides anomalous $\Delta\lambda$ values, for example a high $\Delta\lambda$ value or a statistically significant $\Delta\lambda$ value which is different from the reference region variability, such as an outlier, or a standard deviation which is greater than the remainder of the reference region or normally responding reference region. Another measure provided by the $\Delta\lambda$ map is an image of the surface contours in the microplate well when rendered in color or corresponding gray scale (not shown) where, e.g., a −40 value can represent areas having large negative contour difference(s) and a +40 value represents areas having large positive contour difference(s). The $\Delta\lambda$ map provides a graphic representation of wavelength change or shift, i.e., wavelength difference ($\Delta\lambda$ for the wavelengths measured after microplate development minus the wavelength measured before microplate development. The $\Delta\lambda$ values obtained from the defect region 130 are not representative of the values of the rest of the reference pad and can adversely affect the determined binding value.

Example

Figure 2:
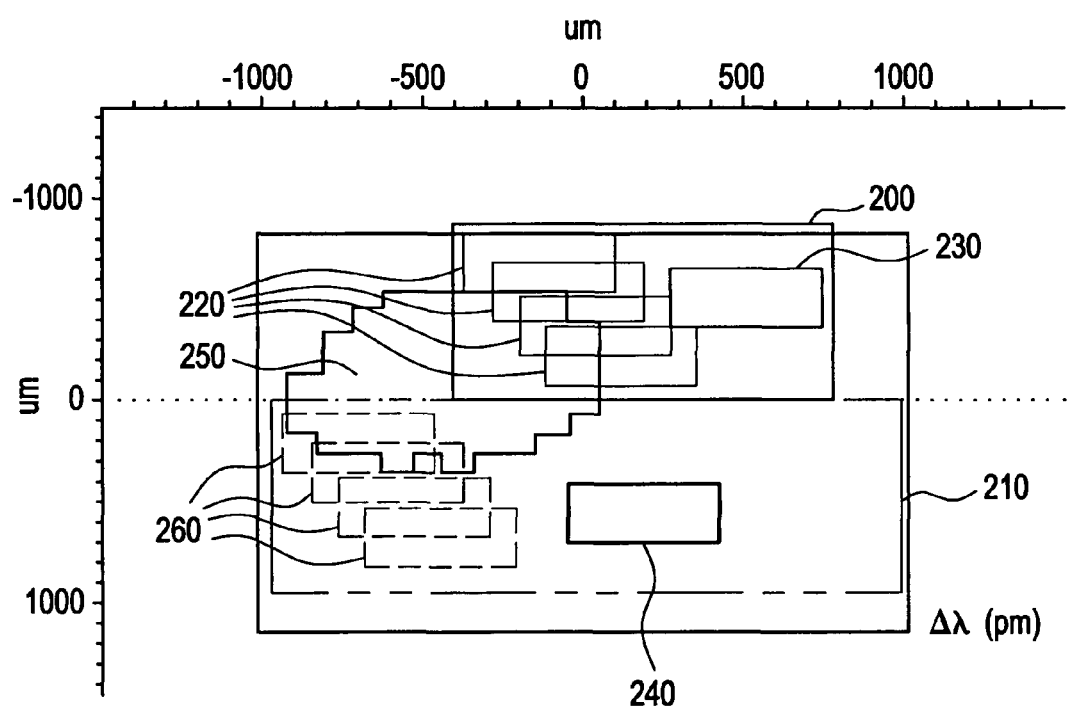
FIG. 2 shows a 2D Δλ map of a well in a microplate showing the areas to be searched for an optimal reference region and an optimal signal region, in embodiments of the disclosure.

2D Sweeping Method In the disclosed 2D sweep method, a two dimensional area of the microplate is scanned at two different time points. The difference in wavelength at each point for these two different time points generates a $\Delta\lambda$ point, that is, where $\Delta\lambda = \lambda_{t2} - \lambda_{t1}$ where $\lambda_{t2}$ and $\lambda_{t1}$ represent the wavelengths measured for the respective second and first time points. After the 2D data collection of these $\Delta\lambda$ points, two "limit" rectangular regions are defined: one for the signal region and one for the reference region. These regions are illustrated for a single well in FIG. 2. Referring to FIG. 2, the rectangle (210) corresponds to the limit signal region and the limit rectangle (200) to the reference region. Next, a size for the "sweeping" rectangles is defined for the reference and signal regions. The size defined for the reference sweeping rectangle is, for example, generally smaller than the size of the reference limit rectangle and similarly for the size of the signal sweeping rectangle. Examples of sweeping rectangles are also illustrated in FIG. 2. The reference sweeping rectangles (220) and the signal sweeping rectangles (260) are shown. The sweep rectangles in the FIG. 2 are shown having approximately the same size. However, the rectangles need not be the same or approximate size, nor the same shape, and can be, for example, any suitable dimension or size, or any suitable shape such as squares, rectangles, parallelograms, trapezoids, and like geometries, or combinations thereof. Thus "rectangle" as used herein includes generic or specific rectangular shapes, and additionally or alternatively, other suitably shaped regions. The sweeping rectangles are allowed, in turn, to occupy all possible locations within their respective limit rectangles provided their borders do not exceed the borders of the respective limit rectangles. For each sweeping rectangle position, the standard deviation of all the $\Delta\lambda$ points it contains is computed. The sweeping rectangle with the smallest standard deviation is deemed the most uniform region. This most uniform region for the reference sweeping rectangles is selected as the reference region that is used for the binding calculation. Similarly, the most uniform region of the signal sweeping region is selected as the signal region that is used for the binding calculation. The binding calculation takes the median value of all $\Delta\lambda$ points in the signal area and subtracts this value from the median value of all $\Delta\lambda$ points in the reference region. In this example it can be seen that a best rectangular region (230) of the reference limit rectangle does not contain any part of the defect region (250). The 2D sweeping routine of the disclosure has the ability to avoid such defects by searching for the region with the lowest standard deviation. In addition, the median binding value, defined as the difference between the medians of the signal and reference regions (rather than the averages), allows even a portion of the defect to be included in the region (230) yet not influence the median binding value unless the defect occupies half or more than half of this region (230).

A function of the optical reader in a Corning Epic® instrument is to measure the resonant wavelengths of a microplate at selected spatial locations. To determine any changes (in time) within each well of a microplate, such as resulting from a ligand-receptor binding event, the difference in resonant wavelengths ($\Delta\lambda$) at each selected spatial location is computed. To remove the contribution of non-biochemical effects, e.g., thermal, bulk index, etc., a non-binding reference region (or pad) can be located and selected within each well. The median binding signal is then determined by finding the difference between the $\Delta\lambda$s of the signal and reference regions. In the unlikely event that the signal and reference regions are each perfectly uniform, then only one value for the binding is obtained regardless of the collection and analysis method chosen. Since variations within the signal and reference regions are unavoidable due to for example variation in manufacture, random surface roughness, extent and variation in binding, or like considerations, the value assigned for the magnitude of any binding event is partly determined by how these points are selected and by how they are analyzed. Therefore, the challenge of any analysis method, which includes selecting a scan pattern and interpreting the resulting data, is to find the most representative binding value for the well. In the comparative one-dimensional (1D) dual-scan method two linear paths of the well were scanned; one for the signal area and one for the reference area. The performance of the 1D method was compared with that of a two-dimensional (2D) sweeping method of the disclosure.

In the disclosed 2D sweeping method, an area of the well is scanned and within this area an optimal or minimized signal region and reference region are located and selected. In addition to improved assay performance, the 2D sweeping method of the disclosure allows wider tolerances on the placement of the reference pad. The disclosed 2D sweeping method is significantly more insensitive to defects in the well compared to the 1D method as discussed below.

Comparing the 1D Dual Scan and 2D Sweeping Methods

The results of the 2D sweeping method are compared with the 1D dual scan method. Since, for example, 10 scans are used for each measurement in the comparative 1D dual scan method, 10 scans were used for the 2D sweeping method. This ensures for the comparison that the total data collection time for both methods was the same. For the 1D measurements, 5 scans, each 672 μm long, were taken in the signal and reference regions. For the 2D analysis, plate maps consisting of 29 scan lines covering the entire grating were used in which 3 of these lines were used for the signal region and 7 were used for the reference region. In this way an actual measurement of 10 scans was simulated. Therefore, the data obtained in this fashion was exactly what would be collected in a 2D, 10 scan measurement. The sweeping rectangles were 3 scan lines by 960 μm in length in the signal region and 5 scan lines by 960 μm in length in the reference area.

For this comparison 15 microplates were analyzed with both the 1D and 2D methods. The standard assay was run on these microplates in which there was a 50/50 mix of positive and negative control wells. The plates were divided into two groups depending on the whether their value of Z' was greater than or less than zero, as determined by the 1D dual scan routine. The Z' values (with and without outliers) and the standard deviations of the positive and negative controls were calculated using, e.g., an Excel macro according to the equation below. In a plot of sampling frequency versus binding a Z' statistic or value can be determined which is a representative measure of the data merit and the overall quality of the assay itself, and is given by the equation:

$$Z'=1-3\{(\sigma_-+\sigma_+)/|\mu_+-\mu_-|\}$$

where
  $\sigma_+$ is the standard deviation for the positive control,
  $\sigma_-$ is the standard deviation for the negative control,
  $\mu_+$ is the measured binding value for the positive control, and
  $\mu_-$ is the measured binding value for the negative control.
See J. Zhang, et al., "A Simple Statistical Parameter for Use in Evaluation and Validation of High Throughput Screening Assays," *Journal of Biomolecular Screening*, Volume 4, Number 2, pp. 67-73, (1999)(see equation (5) page 71 which provides a definition of Z').

In embodiments, Z' can range from minus infinity to plus 1, where for example, and depending on particular experimental circumstances, a positive Z' value such as 0.2 to 0.5 can be considered as good data and a Z' value such as 0.75 to 1.0 can be as considered excellent data. Typical values for $\mu_+$ can be, for example, about 40 and typical values for $\mu_-$ can be, for example, about 0. Typical values for $\sigma_+$ can be, for example, from about 0.1 to about 8 picometers for positive controls, and typical values for $\sigma_-$ can be, for example, from about 0.1 to about 4 picometers for negative controls.

In embodiments, the Z' statistic can alternatively be written as:

$$Z' \equiv 1 - 3\left(\frac{\sigma_{pc} + \sigma_{nc}}{\eta_{pc} - \eta_{nc}}\right)$$

where η and σ represent the mean and standard deviation of the positive control (pc) and negative control (nc) responses, respectively, where the mean difference is taken as the absolute value thereof. A positive control can be, for example, a chemically or biologically modified biosensor surface which has been exposed to a potential assay binding partner. A negative control can be, for example, biosensor surface which has not been a chemically or biologically modified, but has been contacted with only buffer. A "good" system for an assay should provide a Z' value of greater than or equal to about 0.5, with a 1.0 being a perfect Z' value. The results of the first group (11 plates), with Z'>0, are summarized in Table 1 below.

TABLE 1

Z' values calculated with the 1D dual scan method and the 2D sweeping method with and without outliers.

| Plate ID ▼ | Z' 1D, with outliers[1] | Z' 2D with outliers[1] | Z' 1D no outliers[2] | Z' 2D no outliers[2] |
|---|---|---|---|---|
| 1 | 0.82 | 0.80 | 0.83 | 0.80 |
| 2 | 0.77 | 0.76 | 0.86 | 0.82 |
| 3 | 0.66 | 0.62 | 0.83 | 0.81 |
| 4 | 0.61 | 0.76 | 0.76 | 0.78 |
| 5 | 0.58 | 0.78 | 0.76 | 0.78 |
| 6 | 0.56 | 0.71 | 0.60 | 0.72 |
| 7 | 0.54 | 0.57 | 0.72 | 0.76 |
| 8 | 0.47 | 0.47 | 0.69 | 0.81 |
| 9 | 0.44 | 0.50 | 0.49 | 0.53 |
| 10 | 0.40 | 0.39 | 0.45 | 0.48 |
| 11 | 0.16 | 0.28 | 0.16 | 0.28 |
| Average ▶ | 0.55 | 0.60 | 0.65 | 0.69 |

[1]"with outliers" refers to including all data obtained for all wells.
[2]"no outliers" refers to excluding all outlier data obtained for all wells.

Figure 3:
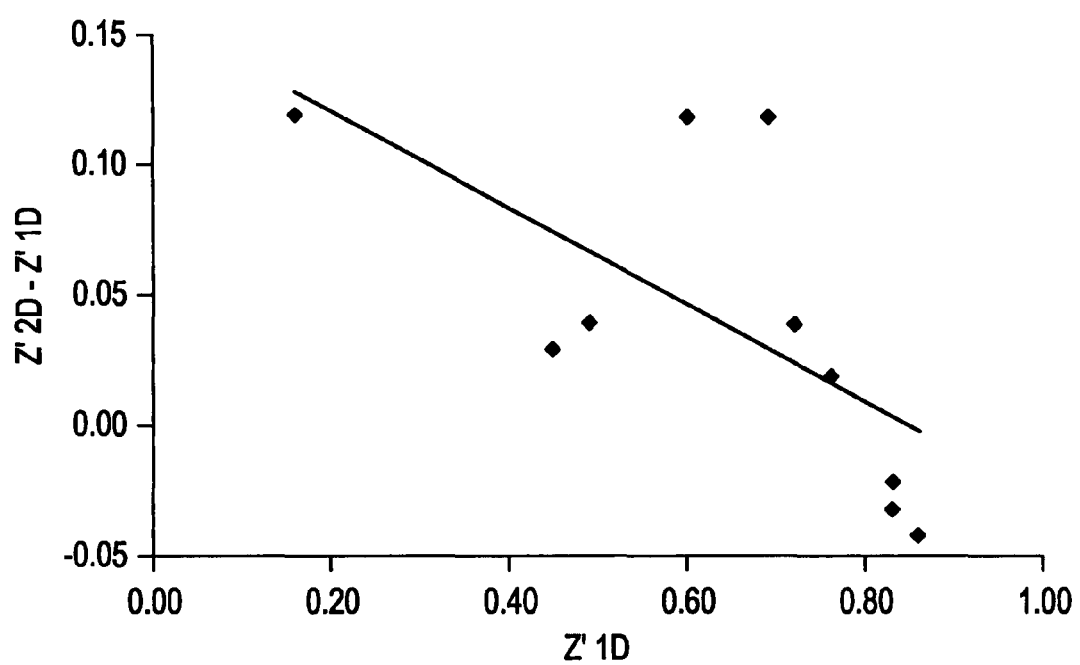
FIG. 3 shows the difference improvement in Z' value or data quality, with the 2D sweeping method as a function of Z' as compared to the 1D dual scan technique, in embodiments of the disclosure.

For microplates with good to excellent performance, the Z' values were about 0.05 higher on average with the 2D analysis. This was true whether or not the outlier wells (i.e., those wells that have anomalously high or low binding values) were included. An outlier well includes both Type I and Type II outliers. A Type I outlier is any well whose binding value lies outside of +/−10× the median average deviation from the distribution average. A Type II outlier is calculated after all Type I outliers are eliminated and is any well whose binding value lies outside of +/−3.5 standard deviations away from the average of this remaining distribution. The standard deviation is also calculated using the remaining distribution. Another important aspect of the disclosed 2D method is that the occurrence of outliers is greatly reduced compared with the 1D method. The 1D results for these 11 plates had a total of 67 outlier wells, as compared with only 56 outliers obtained with the disclosed 2D sweeping method. "Reduced outliers" refers to typical good to excellent outlier diminution or reduction of, for example, about 5 to about 40 percent and from about 10 to about 30 percent for the 2D method compared to the 1D method. Table 1 shows that for a few of the microplates with very high Z' values the 2D method gave a slightly smaller value for Z'. This may be due to the 1D and 2D data collections not being made at the exact same time and so any small time dependent evolution of the binding signal could affect the results. It is interesting to note that the improvement in Z' with the 2D method increases with decreasing Z' value as shown in FIG. 3. This is expected since the lower the Z' value (as measured by the 1D method) the more likely it is that defects or other anomalies exist in the well. Since the 2D method is less sensitive to such defects the improvement in Z' (relative to the 1D result) is expected to increase with increasing numbers of defects. FIG. 3 shows the improvement in Z' with the 2D sweeping method as a function of Z' as measured with the 1D dual scan technique. Although it can be seen in FIG. 3 that while the correlation isn't exact, the predicted trend appears to be supported. The remaining 4 microplates that were analyzed had poor performance (Z'<0) and the results from these plates for the two methods are shown in Table 2.

TABLE 2

Z' values calculated with the 1D dual scan method and the 2D sweeping method with and without outliers for the microplates with poor performance.

| Plate ID | Z' 1D, with outliers | Z' 2D with outliers | Z' 1D no outliers | Z' 2D no outliers |
|---|---|---|---|---|
| 12 | −9.06 | −9.58 | 0.67 | 0.74 |
| 13 | −11.48 | 0.48 | 0.62 | 0.74 |
| 14 | −15.40 | −24.50 | −18.20 | 0.23 |
| 15 | −33.42 | −56.10 | −24.45 | 0.19 |

Here the performance of the plate analysis was improved significantly with the use of the disclosed 2D method. With the 2D method all four plates showed good or excellent performance when outliers were excluded. As with the other 11 microplates, the total number of outliers was reduced from 73 to 52 with the 2D method. The benefit from this reduction in outliers is masked somewhat since the criteria for an outlier depends on the width of the distributions obtained with each method. Another way to appreciate the difference between 1D comparative and the disclosed 2D methods is to examine the standard deviations of the positive and negative controls. For example, Table 3 compares the standard deviations for these controls for the four plates listed in Table 2 (with outliers excluded).

TABLE 3

Standard deviation of the positive and negative controls (in picometers or pm).

| Plate ID | 1D $\sigma_+$ | 2D $\sigma_+$ | 1D $\sigma_-$ | 2D $\sigma_-$ |
|---|---|---|---|---|
| 12 | 3.6 | 2.9 | 1.6 | 1.2 |
| 13 | 4.0 | 2.9 | 1.6 | 1.1 |
| 14 | 300 | 6.7 | 87 | 4.8 |
| 15 | 1113 | 6.9 | 874 | 5.3 |

Here a significant reduction in the variation in these values was enabled by the 2D method. The values in Table 3 do not include the results from outlier wells. The $\sigma_+$ is the standard deviation for the positive control, and $\sigma_-$ is the standard deviation for the negative control.

Figure 4:
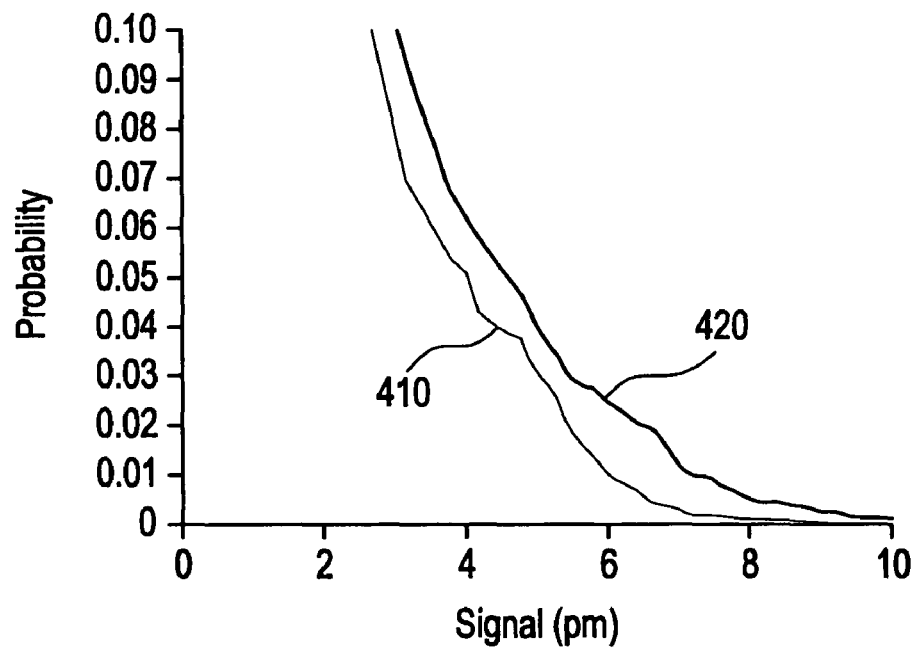
FIG. 4 plots the probability of negative controls and the probability of the occurrence of a false positive for a given signal level, in embodiments of the disclosure.

In the above analysis, the Z' metric was used to determine the quality of the 1D and 2D algorithms. Another important metric is the probability of the occurrence of false negatives and false positives for a given threshold level. In order to determine these probabilities the results from many plates needed to be combined. The 11 microplates that showed the best performance (those listed in Table 1) were used for the analysis that follows concerning this metric. Because the mean values of the positive and negative controls varied considerably from plate to plate, the binding values needed to be scaled before they could be combined in a meaningful way. The scaling that was used caused the negative controls to have a value of 0 pm and the positive controls to have a value of 50 pm for each plate. The scaling was selected so that the Z' values of each plate were preserved. After this scaling was performed, the results from all 11 plates were combined. The overall Z' for the combined 11 plates was 0.50 for the 1D dual scan method and 0.56 for the 2D sweeping method. Next the cumulative probabilities were calculated for the positive and negative controls so that the probabilities of false negatives and false positives, respectively, could be obtained. In FIG. 4, the cumulative probability of the negative controls is plotted for both the 1D dual scan (420) and for the 2D sweeping (410) methods. Here the occurrence of false positives was always significantly greater for the 1D dual scan method. For example, a threshold value of 6 pm shows that the probability of a false positive, that is, a value above 6 pm, was 2.5% using the 1D method but was greatly reduced to a level of about 1% when the 2D analysis was used.

Figure 5:
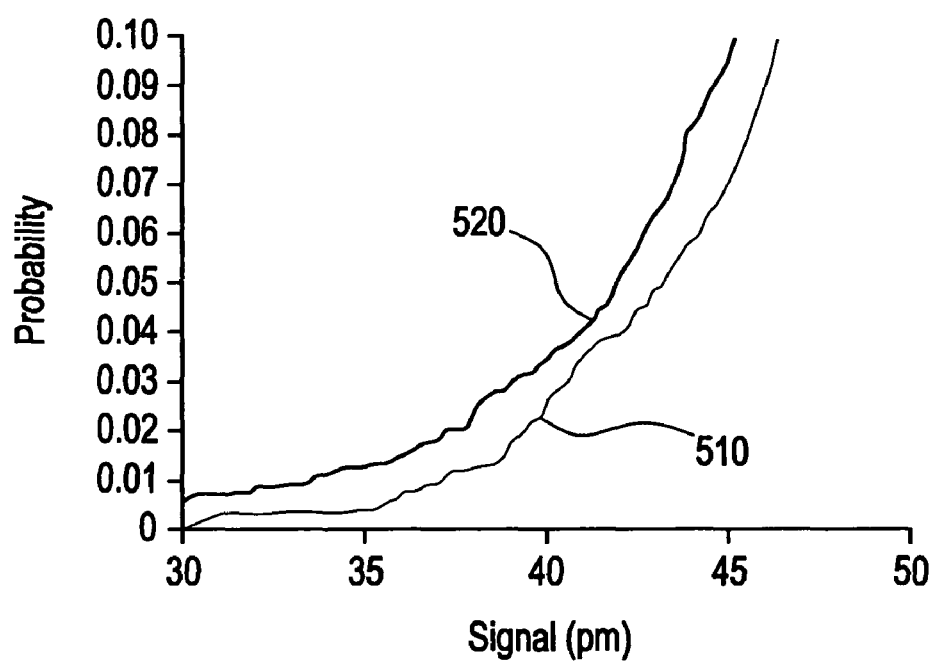
FIG. 5 plots the cumulative probability of the positive controls for both the 1D dual and the 2D sweeping methods and shows the probability of the occurrence of a false negative for a given signal level, in embodiments of the disclosure.

In FIG. 5, the cumulative probability of the positive controls is plotted for both the 1D dual scan (520) and for the 2D sweeping (510) methods. In this instance the occurrence of false negatives was always significantly greater for the 1D dual scan method. For example, at a threshold value of 37 pm the probability of a false negative (that is a value below 37 pm) was 2.0% using the 1D method but was significantly reduced to a level of 1% when the 2D method was used.

Location Tolerance of the Reference Pad

Figure 6:
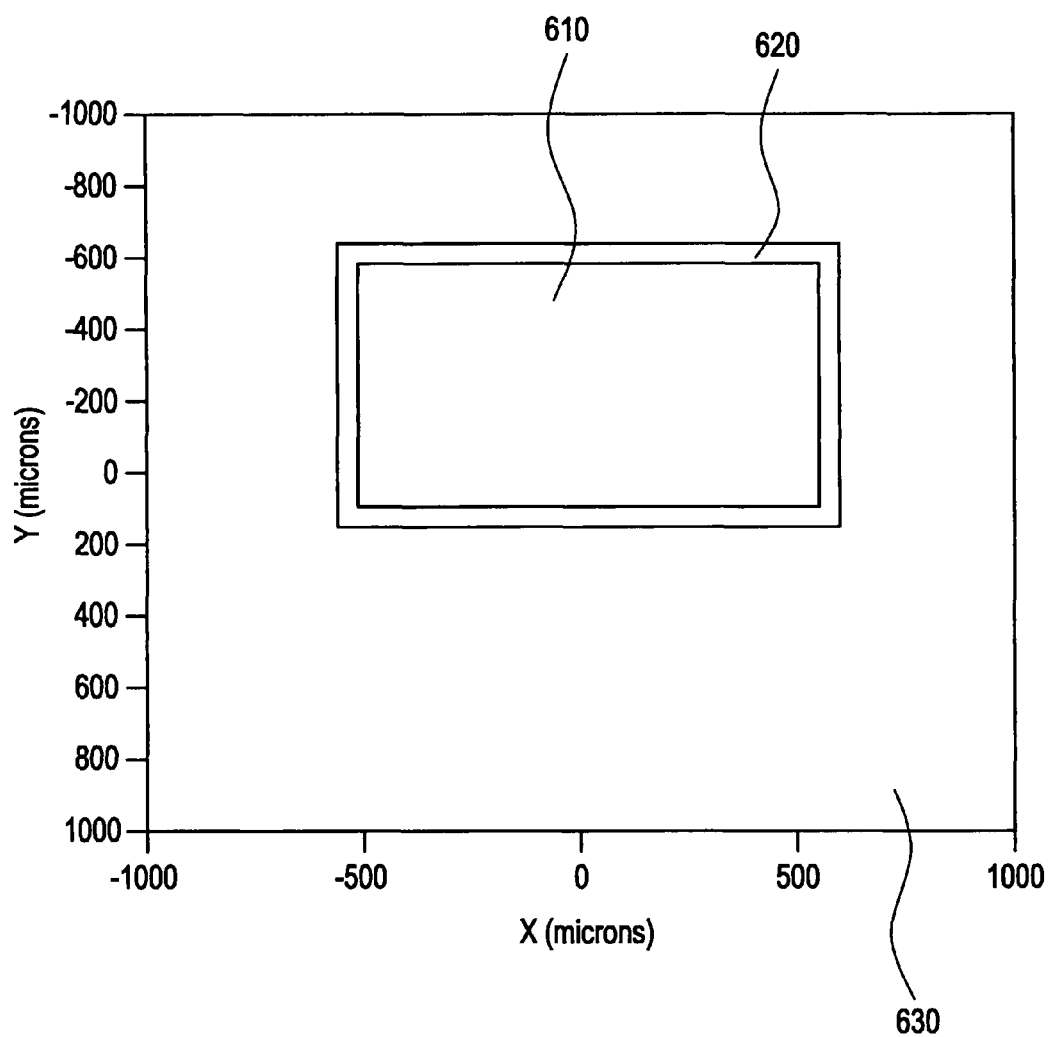
FIG. 6 shows an exemplary reference pad at one location within the 2×2 mm sensor region, in embodiments of the disclosure.

The location of the reference pad must be positioned sufficiently precisely such that an accurate reading is obtained when the pad is scanned. This section compares the size of the allowable region that can be occupied by the center of the reference pad (to get an accurate reading) for the 1D dual scan and 2D sweeping methods. FIG. 6 shows an exemplary reference pad at one location within the 2×2 mm sensor region. For this analysis, the reference pad is assumed to be a perfectly uniform (in $\Delta\lambda$) rectangular region 1,100 microns in x and 650 microns in y. If the scanning beam is located on the edge of the reference pad, it is assumed that the reading will be midway between the signal value and the reference value. Since the scanning beam is 100 microns in diameter, the correct reference value will be obtained provided the center of the scanning beam is in the interior of the pad and at least 50 microns away from the nearest edge. Therefore, to obtain an accurate reference reading, the beam must be within a rectangle whose dimensions are, for example, 1,000 µm in x and 550 µm in y, centered on the physical reference pad. Because of the size of the scanning beam, the response of the reference pad transitions (620) gradually from the reference value (610) to the signal value (630) as shown in FIG. 6.

Figure 7:
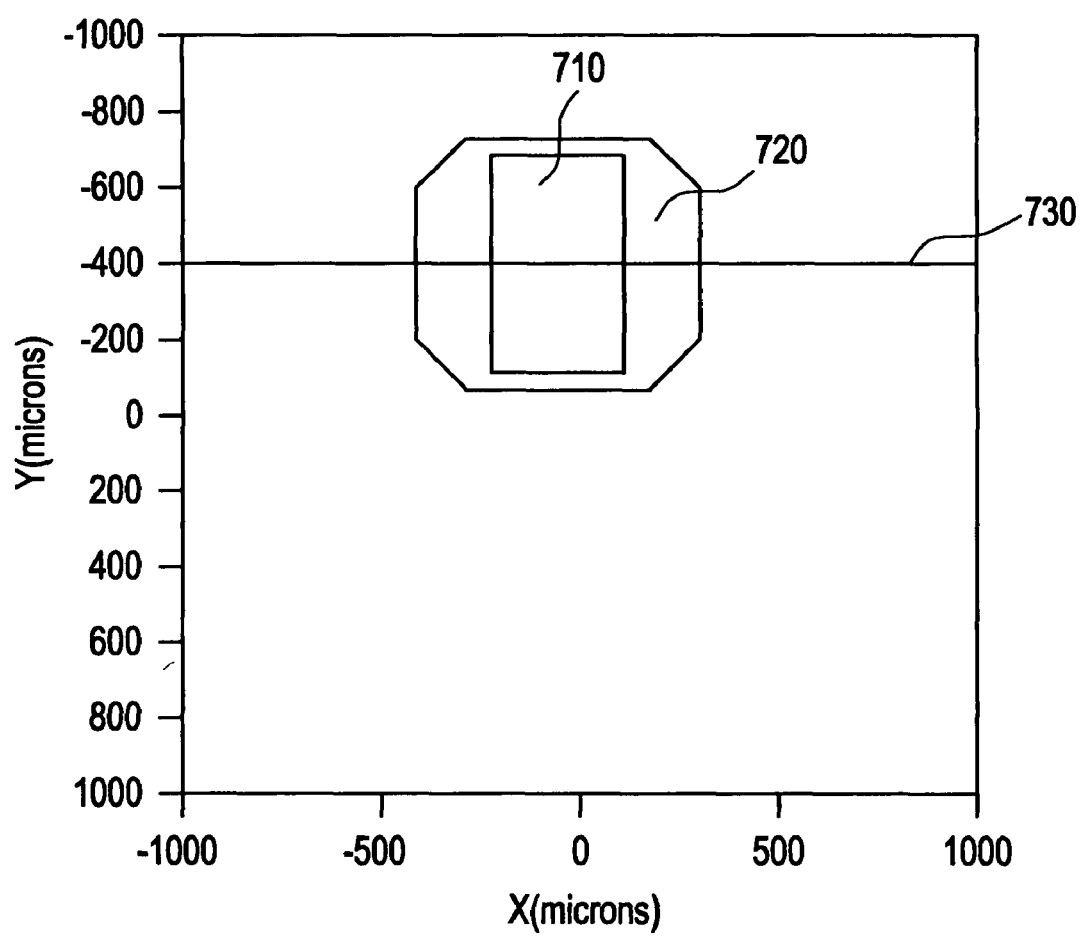
FIG. 7 shows comparative regions that the center of the reference pad can occupy for accurate results for the respective 1D dual scan and 2D sweep methods, in embodiments of the disclosure.

This transition was modeled as a linear change between the reference and signal value, and is a border (620) 100 microns wide surrounding the 1,000×550 microns uniform response rectangle region (610) in FIG. 6 of the reference pad. For the 1D dual scan method, the reference scan consists of a single linear scan in the x-direction of length 672 microns. Since the y-dimension of the uniform region of the reference pad is 550 microns, the center of the reference pad must lie within +/−275 microns in y of this scan line. In the x direction, the center of the reference pad must be within +/−164 microns so that the scan line does not extend outside of the uniform region of the pad. FIG. 7 shows the reference pad center point region (710)(i.e., where the center of the reference region must lie within this region else the analysis will be compromised), 328×550 microns, that the center (730) of the reference pad must occupy for accurate results for the 1D dual scan. FIG. 7 also shows a larger area of non-rectangular region (720), such as an octagon or like non-regular shape having, for example, curved sides, that the reference pad can occupy in the 2D sweep (720) methods.

For the 2D sweep method, seven scan lines spaced approximately 100 microns (µm) apart in y centered on the scan line used in the 1D case were used. The size of the swept region was defined to be 1,000 µm in x by 600 µm in y. The size of the sweep region used was 960 µm×400 µm. The binding value was calculated for all possible positions of the reference pad within the well. The location of the reference pad was always completely contained within the borders of the 2×2 mm sensor area. The result of this calculation is shown as region (720) in FIG. 7. This region (720) represents the allowed location of the center of the reference pad for the 2D sweep method. This region is considerably larger than it is for the 1D dual scan. The maximum dimension in x is +/−400 µm and the maximum dimension in y is +/−325 µm.

In embodiments, the sensor can be spectrally interrogated, that is where the sensor is interrogated at a fixed incidence angle with a broad spectral source and that the wavelength is detected in the reflected beam. The source is then a broad spectral source and the detector is a wavelength sensitive detector such as a spectrometer. In embodiments, however, the sensor can be angularly interrogated where the sensor is interrogated with monochromatic light and then a resonant angle is detected in the reflected beam.

The disclosure has been described with reference to various specific embodiments and techniques. However, it should be understood that many variations and modifications are possible while remaining within the spirit and scope of the disclosure.

What is claimed is:

1. A method for determining biosensor binding, the method comprising:
    scanning an area of the biosensor;
    then in a processor;
        selecting a signal-region and a reference-region within the scanned area;
        scanning at least one sub-region within the signal-region and at least one sub-region within the reference-region;
        calculating a standard deviation for all $\Delta\lambda$ points scanned in each sub-region;
        selecting all sampled points within each of the scanned sub-regions having a minimum standard deviation as a minimum signal sub-region and as a minimum reference sub-region; and
        calculating $M_{sig}$, $M_{ref}$ and $B_{med}$,
    where
        $\Delta\lambda$ is the difference in wavelength for two different time points, according to $\Delta\lambda=\lambda_{t2}-\lambda_{t1}$ where $\lambda_{t2}$ and $\lambda_{t1}$ represent the wavelengths measured for respective second and first time points,
        $M_{sig}$ is the median value of all $\Delta\lambda$ points in the selected minimum signal sub-region,
        $M_{ref}$ is the median value of all $\Delta\lambda$ points in the selected minimum reference sub-region, and
        $B_{med}$ is the median biosensor binding value according to equation (1):

$$B_{med}=M_{sig}-M_{ref} \quad (1).$$

2. The method of claim 1 wherein the biosensor contact surface is undeveloped, developed, or both.

3. The method of claim 1 wherein at least one scanned sub-region within the signal-region and at least one scanned sub-region within the reference-region each has a minimum standard deviation.

4. The method of claim 1 wherein the selected signal-region and the reference-region within the scanned area are mutually exclusive.

5. The method of claim 1 wherein scanning a sub-region within the signal-region and the reference-region comprises a plurality of sub-regions within each of the signal-region and the reference-region.

6. The method of claim 5 wherein the plurality of sub-regions within the signal-region and the reference-region each comprise from about 1 to about 1,000 sub-regions.

7. The method of claim 5 wherein the plurality of sub-regions within the signal-region and the reference-region each comprise from about 10 to about 100 sub-regions.

8. The method of claim 1 wherein the biosensor comprises a plurality of biosensors within a microplate.

9. The method of claim 1 wherein the points of the minimum signal sub-region has a Z' statistic from about 0.6 to about 0.9 when outliers are excluded.

10. The method of claim 1 wherein the dimensions of the signal-region and the reference-region, respectively, are coextensive with, or greater than the dimensions of the respective scanned sub-regions.

11. The method of claim 1 wherein the dimensions of the minimum signal sub-regions and minimum reference sub-regions are less than or equal to, the respective dimensions of the scanned sub-regions.

12. The method of claim 1 wherein the respective dimensions of the signal-region and reference-region are greater than or equal to, the respective dimensions of the signal sub-region and the reference sub-region.

13. The method of claim 1 wherein the respective dimensions of the signal-region and the reference-region have zero height when the selected minimum signal sub-region and selected minimum reference sub-region is less than or equal to the respective signal-region and the reference-region.

14. The method of claim 13 wherein the regions, the sub-regions, or both, reduce to an x-axis scan line.

15. The method of claim 1 wherein the dimensions of a scanned sub-region within the signal region and a scanned sub-region within the reference region have zero height when the selected minimum signal sub-region and selected minimum reference sub-region is less than or equal to the respective signal-region and the reference-region.

16. The method of claim 15 wherein the regions, the sub-regions, or both, reduce to an x-axis scan line.

17. The method of claim 1 wherein at least one scanned sub-region within the signal region and at least one scanned sub-region within the reference region each has a minimum standard deviation.

18. A system to determine biosensor binding, the system comprising:
a microplate comprising a frame including a plurality of wells therein, each well incorporating a biosensor having a surface with a reference region and a sample region;
an optical reader interrogator comprising an optical beam and optics for illuminating a portion of the biosensor, image optics for receiving reflected light from the illuminated biosensor, and a 2D imaging device for capturing a sequence of images from the illuminated biosensor; and
a processor to process the sequence of scanned images in accordance with the method of claim 1 to obtain a biosensor binding value.

19. A method for determining biosensor binding, the method comprising:
scanning an area of the biosensor;
then in a processor:
selecting a signal-region and a reference-region within the scanned area;
scanning at least one sub-region within the signal-region and at least one sub-region within the reference-region;
calculating a standard deviation for all $\Delta\lambda$ points scanned in each sub-region;
selecting all sampled points within each of the scanned sub-regions having a minimum standard deviation as a minimum signal sub-region and as a minimum reference sub-region; and
calculating $A_{sig}$, $A_{ref}$, and $B_{ave}$,
where
$\Delta\lambda$ is the difference in wavelength for two different time points, according to $\Delta\lambda=\lambda_{t2}-\lambda_{t1}$ where $\lambda_{t2}$ and $\lambda_{t1}$ represent the wavelengths measured for respective second and first time points,
$A_{sig}$ is the average value of all $\Delta\lambda$ points in the selected minimum standard deviation signal sub-region,
$A_{ref}$ is the average value of all $\Delta\lambda$ points in the selected minimum standard deviation reference sub-region, and
$B_{ave}$ is the averaged biosensor binding value according to equation (2):

$$B_{ave}=A_{sig}-A_{ref} \qquad (2).$$

20. The method of claim 19 wherein at least one scanned sub-region within the signal region and at least one scanned sub-region within the reference region each has a minimum standard deviation.

* * * * *